United States Patent [19]
Aichinger et al.

[11] Patent Number: 5,396,532
[45] Date of Patent: Mar. 7, 1995

[54] X-RAY DIAGNOSTICS INSTALLATION HAVING MEANS FOR FORMING A TRANSPARENCY SIGNAL

[75] Inventors: Horst Aichinger, Fuerth; Karlheinz Koehler, Herzogenaurach, both of Germany

[73] Assignee: Siemens Aktiengesellschaft, Munich, Germany

[21] Appl. No.: 136,257

[22] Filed: Oct. 15, 1993

[30] Foreign Application Priority Data

Oct. 19, 1992 [DE] Germany ............... 42 35 173.1

[51] Int. Cl.$^6$ .............................. H05G 1/44
[52] U.S. Cl. ................... 378/112; 378/108; 378/111
[58] Field of Search .................. 378/37, 101, 108, 109, 378/110, 111, 112, 114, 117, 97

[56] References Cited

U.S. PATENT DOCUMENTS

| | | |
|---|---|---|
| 4,455,669 | 6/1984 | Aichinger et al. . |
| 4,744,099 | 5/1988 | Huettenrauch et al. ......... 378/37 X |
| 5,148,460 | 9/1992 | Aichinger . |

Primary Examiner—David P. Porta
Attorney, Agent, or Firm—Hill, Steadman & Simpson

[57] ABSTRACT

In an x-ray diagnostics installation for mammography, an automatic setting of the optimum beam quality ensues in combination with transparency matching. A set of exposure parameters corresponding to different thicknesses of the examination subject is stored in a memory (reference values). At the beginning of an x-ray exposure, a comparator compares the transparency signal (actual value) to the exposure parameters (reference value) interrogated from the memory dependent on the current thickness of the examination subject, and influences the x-ray tube voltage for the purpose of a rated/actual value comparison without interrupting the exposure.

1 Claim, 1 Drawing Sheet

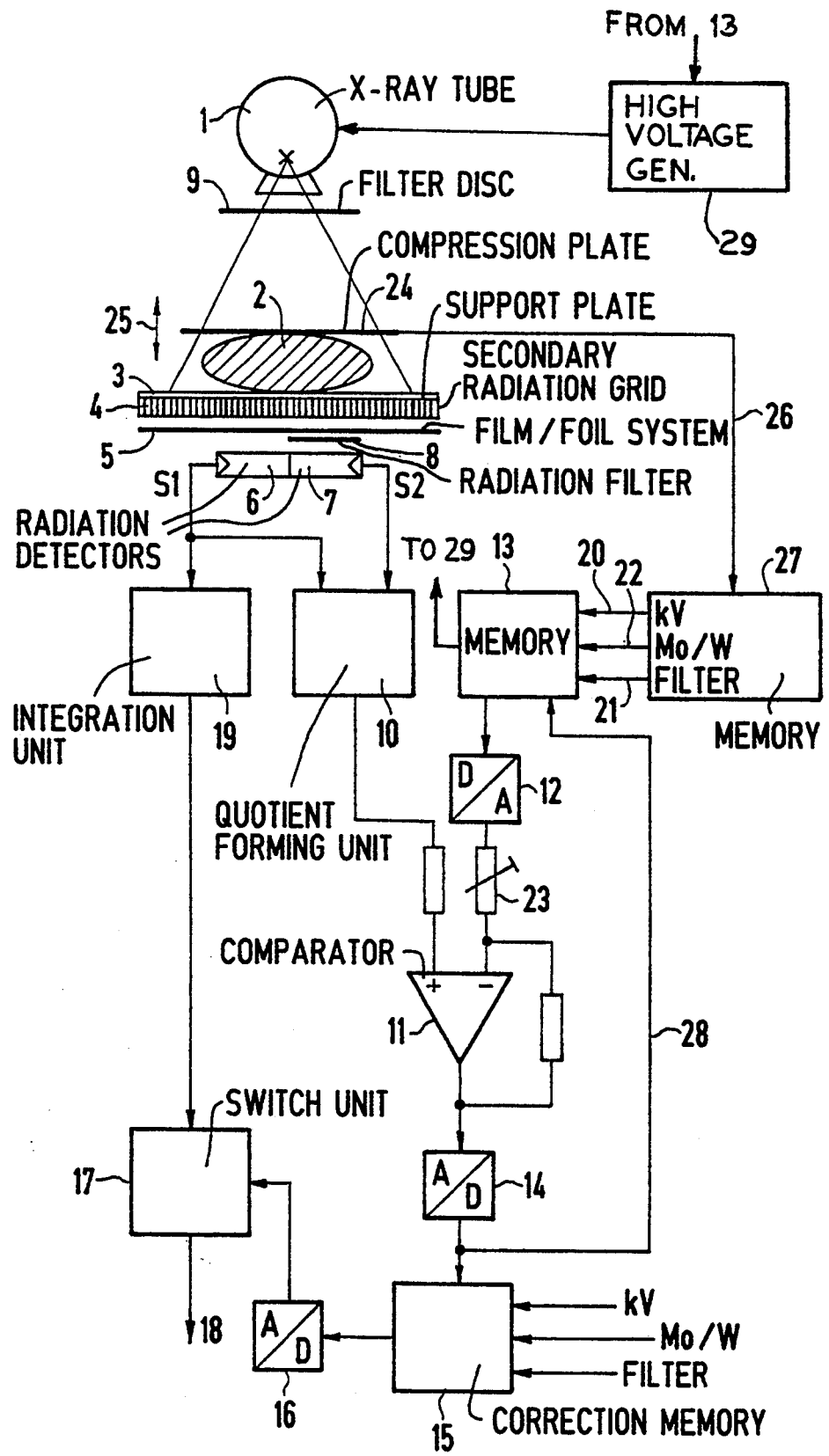

X-RAY DIAGNOSTICS INSTALLATION HAVING MEANS FOR FORMING A TRANSPARENCY SIGNAL

BACKGROUND OF THE INVENTION

1. Field of the Invention

The present invention is directed to an x-ray diagnostics system of the type wherein a transparency signal of the examination subject is used as a basis for setting x-ray exposure parameters.

2. Description of the Prior Art

U.S. Pat. No. 4,455,669 (the teachings of which are incorporated herein by reference) discloses automatic transparency matching, particularly for mammography. This is a technique for controlling the radiation dose by shutting off the x-ray source after a time which is determined in part on a transparency signal of the examination subject, which is representative to the thickness and density of the subject. In this known system the selection of the exposure parameters (kV, filter) ensues manually.

The beam quality (dependent on anode material, filtering, tube voltage) is critical for the image quality obtainable in mammography. The beam quality most frequently employed at present (Mo anode, Mo filter, tube voltage 25 kV through 30 kV) supplies high-contrast images given subjects transparent to radiation. Given thick or dense subjects, the beam exposure is high; moreover, dense gland tissue is only inadequately portrayed. Employing a tube having W-Mo anode dish whose emitted radiation is prefiltered with various cut-off filters (for example, Mo, Ru, Rh) offers one possibility of matching the beam quality to the subject thickness density.

SUMMARY OF THE INVENTION

It is an object of the present invention to provide an x-ray diagnostics installation of the type employing automatic transparency matching wherein the optimum beam quality is automatically set.

This object is inventively achieved in an x-ray diagnostics installation having means for forming a transparency signal for the examination subject, as well as having a memory wherein a set of exposure parameters corresponding to different thicknesses of the examination subject (reference values) are stored. A comparator compares the transparency signal (actual value) to the exposure parameters (reference value) interrogated from the memory dependent on the current thickness of the examination subject. This comparison takes place at the beginning of an x-ray exposure and influences the x-ray tube voltage without interrupting the exposure for the purpose of a rated/actual value matching.

DESCRIPTION OF THE DRAWINGS

The single FIGURE is a block diagram of an x-ray diagnostics system constructed in accordance with the principles of the present invention.

DESCRIPTION OF THE PREFERRED EMBODIMENTS

The drawing shows an x-ray tube 1 having an anode with two focus paths, an Mo path and a W path. X-rays from a selected on of these paths that transirradiate a patient 2 resting on a support plate 3. As viewed in the beam direction, a secondary radiation grid 4 as well as a film/foil system 5 lie behind the support plate 3. Two radiation detectors 6 and 7 are arranged side-by-side behind the film/foil system 5. The radiation detectors 6 and 7 can alternatively be arranged following one another. A beam filter 8, for example a thin copper foil, lies in front of the radiation detector 7. When the detectors 6 and 7 are arranged following one another, the beam filter 8 lies between the detectors 6 and 7. Further, a filter disc 9, for example a rotatable filter disc, is also arranged in the primary beam path preceding the patient 2. The filter disc carries a plurality of radiation filters of, for example, Mo, Ru, Rh that can be individually rotated into the beam path.

The output signals S1 and S2 of the detectors 6 and 7 are supplied to a quotient-forming unit 10 whose output signal is compared in a comparator 11 to an information for a standard thickness and density taken from a memory 13 via a digital-to-analog converter 12. The output signal of the comparator 11, corresponding to the difference of its input signals, is supplied to a correction memory 15 via an analog-to-digital converter 14. The memory 15 supplies a correction signal for every difference signal. The resulting output information of the correction memory 15 determines the shut-off dose of an automatic x-ray exposure unit, and is therefore supplied via a digital-to-analog converter 16 to a switch stage 17 of an automatic exposure unit. The switch stage 17 supplies a shut-off signal at its output 18 when a predetermined radiation dose is achieved at the x-ray film. The automatic exposure unit also contains an integration unit 19.

The transparency information dependent on the radiation transparency and thickness are stored in the memory 13 for all provided exposure values. These values in the memory 13 were previously identified with a calibration measurement. The retrieval of the value required given current conditions ensues on the basis of signals at the inputs 20, 21 and 22. A signal corresponding to the selected x-ray tube voltage is at the input 20, a signal corresponding to the selected filter 9 is at the input 21, and a signal corresponding to the selected focus path is at the input 22. The matching to the various film-foil systems 5 ensues on the basis of information that is supplied to a multiplier resistor 23 of the comparator 11, and correspondingly influences the amplification of the comparator 11 fashioned as a differential amplifier.

The output signal of the digital-to-analog converter 16, which had been formed from the difference signal between the actual radiation transparency and the average radiation transparency given the selected exposure values, modifies the reference value of the shut-off dose dependent on the actual radiation transparency of the exposure subject.

It should be noted that a signal corresponding to the actual transparency or thickness of the exposure subject is formed with the assistance of the two detectors 6 and 7 lying side-by-side in the exemplary embodiment, one of these being covered by the filter 8, and that this signal controls the automatic exposure unit for the purpose of fixing the rated value of the shut-off dose to an optimum value. The illustrated x-ray diagnostics installation is especially suited for mammography exposures, wherein soft x-radiation having x-ray tube voltages between 25 and 40 kV is applied because different radiation transmissivities of the exposure subjects have an especially pronounced effect on the respectively required shut-off dose, given the employment of different film/foil systems.

In the illustrated exemplary embodiment, a radiation filter 8 is arranged in front of one of the detectors, namely in front of the detector 7, whereas there is no corresponding filter in front of the detector 6. This results in respectively different radiation attenuation arising along the radiation paths of the detectors 6 and 7, so that the radiation transparency or thickness of the exposure subject can be calculated from the detector output signals.

A compression plate 24 for compressing the patient 2, such as a breast on the support plate 3, is also shown in the drawing, and is adjustable in the direction of the double arrow 25. Further, a memory 27 is provided for a set of exposure parameters corresponding to different compression thicknesses, and thus Thicknesses of the patient 2. The memory 27 receives a signal corresponding to the compression thickness via the line 26.

Fundamentally, there is no unambiguous relationship between the compression thickness and radiation transparency of the breast. By measuring the compression thickness, however, the overall exposure region can be limited dependent on the subject thickness. One proceeds in the following way: after the compression has been completed, a set of exposure parameters (Mo anode or W anode, kV, filter) allocated to the compression thickness is preselected in the memory 27 and preset. The allocation of the exposure parameters (in the memory 27) to object thickness ranges can be determined by the radiologist. For example:

| Object thickness: | 2-3 mm | >3-4 cm | >4-6 cm | >6 cm |
|---|---|---|---|---|
| Exposure: parameters: | Mo focal spot | Mo focal spot | Mo focal spot | W focal spot |
| | 26 kV | 26 kV | 29 kV | 29 kV |
| | Mo filter | Ru filter | Rh filter | Rh filter |

A reference quotient S2/S1 is allocated to these thickness ranges in the memory 13.

After the exposure has been triggered and the high-voltage has built up, the S2/S1 actual value is identified in the quotient-forming unit 10 and is compared to the rated value in the comparator 11. Given coincidence, the x-ray exposure is ended, and the corresponding correction signal for the transparency matching of the automatic exposure unit is provided via the output of the correction memory 15.

Given deviation of reference value from actual value, the correct beam quality is identified by supplying the difference signal to the memory 13 via a return line 28. A change of focal spot or filter would ordinarily require an interruption of the exposure required. The goal of the present system, however, is to operate without a test shot and without interrupting the ongoing exposure. During the ongoing exposure, only the tube voltage is therefore raised or lowered by a signal from the memory 13 to the high-voltage generator 29, dependent on the signal received by the memory 13 from line 28, in order to achieve a corresponding beam quality. After the change of the voltage has been carried out, the correction signal for the transparency matching is again identified and the exposure is completed.

In general, a transparency signal for the examination subject 2 is formed with the quotient-forming unit 10. A set of exposure parameters corresponding to different thicknesses of the examination subject 2 (reference values) is stored in the memory 27. At the beginning of an x-ray exposure, the comparator 11 compares the transparency signal (actual value) of the quotient-forming unit 10 to the exposure parameters (reference value) interrogated from the memory 27 dependent on the current thickness of the examination subject 2. The x-ray tube voltage is influenced for the purpose of rated-/actual value matching without interrupting the exposure.

Although modifications and changes may be suggested by those skilled in the art, it is the intention of the inventors to embody within the patent warranted hereon all changes and modifications as reasonably and properly come within the scope of their contribution to the art.

We claim as our invention:

1. An x-ray diagnostics installation comprising:
   means, including an x-ray tube operating at an x-ray tube voltage, for forming a transparency signal of an examination subject and for thereafter conducting an x-ray exposure of said examiner subject;
   memory means for storing a set of exposure parameters corresponding to different examination subject thicknesses;
   means for interrogating said memory means;
   comparator means for, at a beginning of an x-ray exposure, comparing said transparency signal to said sets of exposure perameters interrogated from said memory means dependant on the thickness of said examination subject for selecting a set of exposure perameters best matched to said thickness of said examination subject; and
   means for adjusting said x-ray tube voltage to correspond to the selected set of perameters without interrupting said x-ray exposure.

* * * * *